(12) United States Patent
Mattke et al.

(10) Patent No.: US 8,916,725 B2
(45) Date of Patent: Dec. 23, 2014

(54) PROCESS FOR PREPARING ISOCYANATES

(75) Inventors: Torsten Mattke, Freinsheim (DE); Carsten Knösche, Niederkirchen (DE)

(73) Assignee: BASF SE, Ludwigshafen (DE)

( * ) Notice: Subject to any disclaimer, the term of this patent is extended or adjusted under 35 U.S.C. 154(b) by 472 days.

(21) Appl. No.: 13/128,104

(22) PCT Filed: Nov. 4, 2009

(86) PCT No.: PCT/EP2009/064578
§ 371 (c)(1),
(2), (4) Date: May 6, 2011

(87) PCT Pub. No.: WO2010/052230
PCT Pub. Date: May 14, 2010

(65) Prior Publication Data
US 2011/0213178 A1 Sep. 1, 2011

(30) Foreign Application Priority Data
Nov. 7, 2008 (EP) .................................... 08168617

(51) Int. Cl.
*C07C 263/10* (2006.01)
(52) U.S. Cl.
CPC .................................... *C07C 263/10* (2013.01)
USPC ......................................................... 560/347
(58) Field of Classification Search
CPC .................................................... C07C 263/10
USPC ......................................................... 560/347
See application file for complete search history.

(56) References Cited

U.S. PATENT DOCUMENTS

| 7,488,842 | B2 * | 2/2009 | Knoesche | ..................... 560/347 |
| 2008/0146834 | A1 | 6/2008 | Pohl et al. | |
| 2008/0167490 | A1 | 7/2008 | Pohl et al. | |
| 2010/0076218 | A1 | 3/2010 | Daiss et al. | |

FOREIGN PATENT DOCUMENTS

| DE | 10 2006 058 634 | 6/2008 | |
| EP | 1 319 655 | 6/2003 | |
| EP | 1 403 248 | 3/2004 | |
| EP | 1 555 258 | 7/2005 | |
| EP | 1 935 875 | 6/2008 | |
| EP | 1 935 876 | 6/2008 | |
| WO | WO 2005/123665 | * 12/2005 | ............ C07C 263/10 |
| WO | 2007 028715 | 3/2007 | |
| WO | 2008 055899 | 5/2008 | |

OTHER PUBLICATIONS

Copending U.S. Appl. No. 13/123,787.*
International Search Report issued May 25, 2010 in PCT/EP09/064578 filed Nov. 4, 2009.

* cited by examiner

*Primary Examiner* — Rosalynd Keys
(74) *Attorney, Agent, or Firm* — Oblon, Spivak, McClelland, Maier & Neustadt, L.L.P.

(57) ABSTRACT

The invention relates to a process for preparing isocyanates by reacting the corresponding amines with phosgene in the gas phase, if appropriate in the presence of an inert medium, in which the amine and the phosgene are first mixed and converted to the isocyanate in a reactor, by cooling a reaction gas which comprises isocyanate and hydrogen chloride and leaves the reactor in a quench by adding a liquid quench medium to obtain a mixture of reaction gas and quench medium. The amount of quench medium added is such that the temperature of the mixture of reaction gas and quench medium which is established in the quench is above the dew point of the gas present in the quench.

14 Claims, No Drawings

PROCESS FOR PREPARING ISOCYANATES

CROSS REFERENCE TO RELATED APPLICATION

This application is a 371 of PCT/EP2009/064578, filed on Nov. 4, 2009, and claims priority to European Patent Application No. 08168617.2, filed on Nov. 7, 2008.

The invention proceeds from a process for preparing isocyanates by reacting the corresponding amines with phosgene in the gas phase, if appropriate in the presence of an inert medium, in which the amine and the phosgene are first mixed and converted to the isocyanate in a reactor, by cooling a reaction gas which comprises isocyanate and hydrogen chloride and leaves the reactor in a quench apparatus by adding a liquid quench medium to obtain a mixture of reaction gas and quench medium.

The preparation of isocyanates by phosgenating the corresponding amines can in principle be effected by a liquid phase or gas phase phosgenation. Gas phase phosgenation is notable in that a higher selectivity is possible and a smaller holdup of toxic phosgene and a reduced energy demand are required.

In gas phase phosgenation, an amine-containing reactant stream and a phosgene-containing reactant stream, each in the gaseous state, are mixed. The amine and the phosgene react to give the corresponding isocyanates with release of hydrogen chloride (HCl). The amine-containing reactant stream is generally present in the liquid phase and has to be evaporated and if appropriate superheated before being mixed with the phosgene-containing stream.

Corresponding processes for preparing isocyanates in the gas phase are described, for example, in EP-A 1 319 655 or EP-A 1 555 258.

In order to prevent further reactions, it is necessary to cool the reaction mixture rapidly after the end of the reaction. To this end, for example, a liquid quench is used. Such a liquid quench is described, for example, in EP-A 1 403 248 or in DE-A 10 2006 058 634. The quench medium which is added for cooling has a temperature which is in the range from 50 to 200° C. The liquid stream sprayed in cools the reaction gas rapidly to temperatures generally between 100 and 200° C. This forms a biphasic mixture with an isocyanate-rich liquid phase and a low-isocyanate gas phase. Both are subsequently fed to a combined or if appropriate separate separating stage, for example a distillation stage for separation of hydrogen chloride and phosgene on the one hand, and isocyanate on the other hand.

A disadvantage of the known apparatus for quenching is, however, that some wall regions within the quench apparatus have low liquid wetting. At these points, the reaction mixture which condenses out can reside for a long period and undergo further reactions which have an adverse effect on the selectivity of the overall process. In addition, components which sublime, or else solids which form through further reactions, can lead to deposits and thus have an adverse effect on the run time of the plant. A further problem is the formation of aerosols. These are ultrafine droplets or particles which form through the rapid cooling of the gas phase. These aerosols can pass through the subsequent separating processes with the gas phase and reduce the separating action thereof. It is therefore necessary to remove the droplets by appropriate technical measures.

It is thus an object of the present invention to provide a process for preparing isocyanates by reacting the corresponding amines with phosgene, in which aerosol formation and deposits in the quench space are prevented.

The object is achieved by a process for preparing isocyanates by reacting the corresponding amines with phosgene in the gas phase, if appropriate in the presence of an inert medium, in which the amine and the phosgene are first mixed and converted to the isocyanate in a reactor, by cooling a reaction gas which comprises isocyanate and hydrogen chloride and leaves the reactor in a quench by adding a liquid quench medium to obtain a mixture of reaction gas and quench medium. The amount of quench medium added is such that the temperature of the mixture of reaction gas and quench medium which is established in the quench is above the dew point of the gas present in the quench.

By virtue of the quench medium being adjusted such that the temperature of the mixture of reaction gas and quench medium is above the dew point of the gas present in the quench, no aerosols can form. No constituents of the mixture of reaction gas and quench medium condense out, and no components desublime.

By virtue of the prevention of aerosol formation, it is additionally unnecessary that the gas must pass through a separation process in which aerosols are removed downstream of the quench. In addition, the separating action of separating processes for removing the isocyanate from the mixture in separating processes which follow downstream of the quench is not reduced.

To prepare the isocyanate, the phosgene and the amine are preferably first fed to a mixing zone in which amine and phosgene are mixed to give a reaction mixture. Subsequently, the reaction mixture is fed to the reactor in which the conversion to the isocyanate is effected. The reaction of amine and phosgene in the reactor is preferably effected in the gas phase. The pressure in the reactor is preferably in the range between 0.3 and 3 bar absolute, especially preferably in the range from 0.8 to 3.0 bar absolute. The temperature is preferably in the range from 250 to 550° C., especially in the range from 300 to 500° C.

In order to be able to perform the reaction in the gas phase, it is additionally preferred to add the amine and the phosgene in gaseous form. To this end, the amine preferably has a temperature in the range from 200 to 400° C. The pressure of the amine added is preferably in the range between 0.05 and 3 bar absolute. The temperature of the phosgene added is preferably in the range from 250 to 450° C. To this end, the phosgene is typically heated in the manner known to those skilled in the art before addition.

To heat the phosgene and the amine and to evaporate the amine, for example, an electrical heater or direct or indirect heating by combustion of a fuel is used. The fuels used are typically fuel gases, for example natural gas. However, by virtue of the lowering of the boiling temperature by lowering the pressure of the amine, heating is also possible, for example by means of steam. The pressure of the steam is selected here as a function of the boiling temperature of the amine. A suitable vapor pressure of the steam is, for example, in the range from 40 to 100 bar. This gives rise to a temperature of the steam in the range from 250 to 311° C.

In general, it is necessary to heat the amine to the reaction temperature in several stages. In general, the amine is first preheated for this purpose, then evaporated and subsequently superheated. In general, the evaporation entails the longest residence times and thus leads to decomposition of the amine. In order to minimize this, evaporation at lower temperatures, as arise, for example, through the lower pressure, is advantageous. In order to superheat the evaporated amine to reaction temperature after the evaporation, heating with steam is generally insufficient. An electrical heater or direct or indirect heating by combustion of a fuel is therefore typically used for superheating.

In contrast to the evaporation of the amine, the evaporation of the phosgene is generally effected at significantly lower temperatures. For this reason, the phosgene can generally be evaporated using steam. However, the necessary superheating of the phosgene in order to heat it to reaction temperature is also generally possible only by means of electrical heating or direct or indirect heating by combustion of a fuel.

The reactor which is used for phosgenation of the amine to prepare isocyanates is known to those skilled in the art. In general, the reactors used are tubular reactors. In the reactor, the amine is reacted with the phosgene to give the corresponding isocyanate and hydrogen chloride. Typically, the phosgene is added in excess, such that the reaction gas formed in the reactor, as well as the isocyanate formed and the hydrogen chloride, also comprises phosgene.

Amines which can be used to prepare isocyanates are monoamines, diamines, triamines or higher-functionality amines. Preference is given to using monoamines or diamines. According to the amine used, the corresponding monoisocyanates, diisocyanates, triisocyanates or higher-functionality isocyanates are obtained. Preference is given to preparing monoisocyanates or diisocyanates by the process according to the invention.

Diamines and diisocyanates may be aliphatic, cycloaliphatic or aromatic. The amines are preferably aliphatic or cycloaliphatic, more preferably aliphatic.

Cycloaliphatic isocyanates are those which comprise at least one cycloaliphatic ring system.

Aliphatic isocyanates are those which have exclusively isocyanate groups which are bonded to straight or branched chains.

Aromatic isocyanates are those which have at least one isocyanate group bonded to at least one aromatic ring system.

The term "(cyclo)aliphatic isocyanates" is used hereinafter for cycloaliphatic and/or aliphatic isocyanates.

Examples of aromatic mono- and diisocyanates are preferably those having 6 to 20 carbon atoms, for example phenyl isocyanate, monomeric 2,4'- and/or 4,4'-methylenedi-(phenyl isocyanate) (MDI), 2,4- and/or 2,6-tolylene diisocyanate (TDI) and/or 1,5- or 1,8-naphthyl diisocyanate (NDI).

Examples of (cyclo)aliphatic diisocyanates are aliphatic diisocyanates such as 1,4-tetramethylene diisocyanate, 1,6-hexamethylene diisocyanate (1,6-diiso-cyanatohexane), 1,8-octamethylene diisocyanate, 1,10-decamethylene diisocyanate, 1,12-dodecamethylene diisocyanate, 1,14-tetradecamethylene diisocyanate, 1,5-diisocyanatopentane, neopentane diisocyanate, derivatives of lysine diisocyanate, tetramethylxylylene diisocyanate (TMXDI), trimethylhexane diisocyanate or tetramethylhexane diisocyanate, and 3 (or 4), 8(or 9)-bis(isocyanatomethyl)tricyclo-[5.2.1.0$^{2,6}$]decane isomer mixtures, and cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane, 2,4- or 2,6-diisocyanato-1-methylcyclohexane.

Preferred (cyclo)aliphatic diisocyanates are 1,6-diisocyanatohexane, 1-isocyanato-3,3,5-trimethyl-5-(isocyanatomethyl)cyclohexane, 4,4'-di(isocyanatocyclohexyl)-methane and tolylene diisocyanate isomer mixtures. Particular preference is given to 1,6-diisocyanatohexane, 1-isocyanato-3,3,5-trimethyl-5-(isocyanatomethyl)cyclohexane and 4,4'-di(isocyanatocyclohexyl)methane.

Amines which are used in the process according to the invention for reaction to give the corresponding isocyanates are those in which the amine, the corresponding intermediates and the corresponding isocyanates are present in gaseous form under the selected reaction conditions. Preference is given to amines which decompose over the duration of the reaction under the reaction conditions to an extent of at most 2 mol %, more preferably to an extent of at most 1 mol % and most preferably to an extent of at most 0.5 mol %. Particularly suitable amines here are especially diamines based on aliphatic or cycloaliphatic hydrocarbons having 2 to 18 carbon atoms. Examples thereof are 1,6-diaminohexane, 1,5-diaminopentane, 1,3-bis(amino-methyl)cyclohexane, 1-amino-3,3,5-trimethyl-5-aminomethylcyclohexane (IPDA) and 4,4-diaminodicyclohexylmethane. Preference is given to using 1,6-diaminohexane (HDA).

It is likewise possible to use aromatic amines which can be converted to the gas phase without significant decomposition for the process according to the invention. Examples of preferred aromatic amines are tolylenediamine (TDA), as the 2,4 or 2,6 isomer or as a mixture thereof, for example as an 80:20 to 65:35 (mol/mol) mixture, diaminobenzene, 2,6-xylidine, naphthyldiamine (NDA) and 2,4'- or 4,4'-methylene(diphenyldiamine) (MDA) or isomer mixtures thereof. Among these, preference is given to the diamines, particular preference to 2,4- and/or 2,6-TDA or 2,4'- and/or 4,4'-MDA.

To prepare monoisocyanates, aliphatic, cycloaliphatic or aromatic amines, typically monoamines, can also be used. An especially preferred aromatic monoamine is aniline.

In the gas phase phosgenation, it is desirable that the compounds which occur in the course of the reaction, i.e. reactants (amine and phosgene), intermediates (especially the mono- and dicarbamoyl chlorides which form as intermediates), end products (diisocyanate), and any inert compounds metered in, remain in the gas phase under the reaction conditions. Should these or other components be deposited from the gas phase, for example on the reactor wall or other apparatus components, these depositions can undesirably alter the heat transfer or the flow through the components involved. This is especially true of occurrence of the amine hydrochlorides, which form from free amino groups and hydrogen chloride, since the resulting amine chlorides precipitate out readily and are reevaporable only with difficulty.

In addition to the use of a tubular reactor, it is also possible to use essentially cuboidal reaction chambers, for example plate reactors. Any other desired cross section of the reactor is also possible.

In order to prevent the formation of by-products, it is preferred to supply phosgene in excess. In order to supply only the proportion of amines needed for the reaction, it is possible to mix the amine with an inert gas. Through the proportion of the inert gas in the amine, it is possible to adjust the amount of amine supplied for a given geometry of the feed orifices for the amine and the phosgene. Inert media which can be added are those which are present in gaseous form in the reaction chamber and do not react with compounds which occur in the course of the reaction. The inert media used may, for example, be nitrogen, noble gases such as helium or argon, aromatics such as chlorobenzene, o-dichlorobenzene, trichlorobenzene, toluene, xylene, chloronaphthalene, decahydronaphthalene, carbon dioxide or carbon monoxide. Preference is given, however, to using nitrogen and/or chlorobenzene as the inert medium.

Alternatively, however, it is also possible, for example, in order to avoid too great an excess of phosgene, to add the phosgene to the inert medium.

In general, the inert medium is added in an amount such that the ratio of the gas volumes of inert medium to amine or to phosgene is less than 0.0001 to 30, preferably less than 0.01 to 15 and more preferably less than 0.1 to 5.

In order to reduce or to prevent the formation of undesired by-products and additionally also to suppress decomposition of the isocyanate formed, the reaction gas is cooled in a quench immediately after the reaction. To this end, a preferably liquid quench medium is added. As a result of evaporation of the quench medium, it absorbs heat, which leads to rapid cooling of the reaction gas.

In order to prevent reaction products or reaction by-products or quench medium from condensing out or desubliming and thus forming aerosols in the mixture, the amount of quench medium which is added is such that the mixing temperature which is established from reaction gas and quench medium is above the dew point of this gas mixture. It is necessary for this purpose that the partial pressure for all components present in the gas mixture is less in each case than the vapor pressure thereof. At the dew point, the partial pressure of at least one component just reaches the vapor pressure thereof.

The quench medium is generally added in liquid form. The temperature of the quench medium is preferably in the range from 0 to 250° C., especially in the range from 20 to 220° C. The spraying of the quench medium into the hot reaction gas heats and evaporates the quench medium. The heat needed for the heating and the evaporation of the quench medium is taken from the reaction gas, and the reaction gas is cooled in this way. By virtue of the amount of the quench medium added being such that the temperature of the mixture of reaction gas and quench medium is above the dew point of this mixture, it is ensured that all of the quench medium evaporates and droplets of quench medium do not remain in the reaction gas.

In one embodiment, the quench medium is added via at least one nozzle.

A suitable quench medium is an optionally halogen-substituted hydrocarbon. Preferably, the quench medium is selected from the group consisting of monochlorobenzene, dichlorobenzene, trichlorobenzene, hexane, benzene, 1,3,5-trimethylbenzene, nitrobenzene, anisole, chlorotoluene, o-dichlorobenzene, diethyl isophthalate, tetrahydrofuran, dimethylformamide, xylene, chloronaphthalene, decahydronaphthalene and toluene.

In one embodiment of the invention, the quench may be followed by further stages for cooling the reaction gas. In the individual stages for cooling, the reaction gas is cooled further in each case until attainment of the desired end temperature, with which the reaction gas is fed, for example, to a downstream workup.

The further stages for cooling, which may follow the quench, may, for example, be further quenches or condensers or any other stages for cooling which are known to those skilled in the art. At least one of the stages for cooling the reaction gas which follow the quench is preferably a condenser. Suitable condensers are any desired condenser designs known to those skilled in the art. Typically, the condenser used is a heat exchanger through which a cooling medium flows. The coolant used may, for example, be water. In this case, the gas condenses at least partly from the walls of the condenser. The liquid thus formed runs off and is collected and withdrawn from the condenser.

The condensing of the mixture of reaction gas and quench medium is generally followed downstream by a workup. For example, it is possible that the mixture condensed out is washed in a solvent. The solvents used may, for example, be the same substances which can also be used as the quench medium.

In the scrubbing, the isocyanate is transferred selectively to the scrubbing solution. Subsequently, the resulting mixture is separated, preferably by rectification, into isocyanate, solvent, phosgene and hydrogen chloride.

Alternatively to the cooling and condensation of the mixture of quench medium and reaction gas, it is also possible that the mixture of reaction gas and quench medium is fed to a separating stage after leaving the quench. A corresponding separating stage can alternatively, however, also follow the condenser, for example. However, the separating stage preferably directly follows the quench. Suitable separating stages are, for example, distillation columns or scrubbers.

When the separating stage is a scrubber, the mixture of reaction gas and quench medium which leaves the quench is preferably—as described above—washed with a solvent. This transfers the isocyanate selectively into the scrubbing solution. The scrubbing is then followed by a separation, preferably by means of rectification.

When the separating stage is a distillation column, the gaseous mixture of reaction gas and quench medium is fed to the rectification column. The rectification column is operated in such a way that the temperature at the top of the rectification column is lower than the boiling temperature of the mixture of quench medium and reaction gas. In this way, individual constituents of the mixture of quench medium and reaction gas condense out selectively in the distillation column and can be withdrawn from the column at the bottom, via the top and if appropriate via side draws.

When the separating stage is a scrubber, a scrubbing tower is especially suitable, in which the isocyanate formed is removed by condensation in an inert solvent from the gaseous mixture of reaction gas and quench medium, while excess phosgene, hydrogen chloride and if appropriate the inert medium pass through the scrubbing tower in gaseous form. The temperature of the inert solvent is preferably kept above the dissolution temperature of the carbamoyl chloride corresponding to the amine in the selected scrubbing medium. The temperature of the inert solvent is especially preferably kept above the melting temperature of the carbamoyl chloride corresponding to the amine.

Suitable scrubbers are any desired scrubbers known to those skilled in the art. For example, it is possible to use stirred vessels or other conventional apparatus, for example columns or mixer-settler apparatus.

The scrubbing and the workup of the mixture of reaction gas and quench medium leaving the quench are generally effected as described, for example, in WO-A 2007/028715.

EXAMPLE

In a reactor for phosgenating amines to prepare isocyanates, approx. 1.8 kg/h of tolylenediamine are phosgenated. The phosgene required for phosgenation is supplied in excess. This forms 15.95 kg/h of a reaction gas which has a temperature of 458° C. The reaction gas comprises 15.7% by weight of tolylene diisocyanate, 71.2% by weight of phosgene and 13.1% by weight of hydrogen chloride. The reaction gas is cooled in a quench with 7.5 kg/h of monochlorobenzene as the quench medium. The monochlorobenzene is supplied in liquid form with a temperature of 60° C. via a spray nozzle. In the quench, there is a pressure of 2 bar absolute. The mixing temperature which is established in the quench is approx. 195° C. Since the dew point of the reaction gas is 183° C. and that of the gaseous quench output is 178° C., the mixture of reaction gas and quench medium leaving the quench remains in gaseous form, without aerosols forming. This allows the quench to be operated without disruption over a long period of time. With the aid of a sightglass, the quench output was studied for aerosols. No aerosols could be detected in the quench output.

The invention claimed is:

1. A process for preparing isocyanates, comprising:
   mixing an amine and phosgene in a reactor;
   reacting the amine with phosgene in the gas phase, optionally in the presence of an inert medium, thereby forming a reaction gas that comprises an isocyanate and hydrogen chloride; and
   contacting the reaction gas which comprises the isocyanate and hydrogen chloride with a liquid quench medium, thereby cooling the reaction gas and obtaining a mixture of the reaction gas and the quench medium, each in gaseous form,
   wherein the amount of quench medium added is such that the temperature of the mixture of reaction gas and quench medium which is established in the quench is above the dew point of the gas mixture present in the quench.

2. The process according to claim 1, wherein, during said mixing, the amine and the phosgene are each in gaseous form.

3. The process according to claim 1, wherein the quench medium is added via at least one nozzle.

4. The process according to claim 1, wherein the quench medium is an optionally halogen-substituted hydrocarbon.

5. The process according to claim 1, wherein the quench medium is selected from the group consisting of monochlorobenzene, dichlorobenzene, trichlorobenzene, hexane, benzene, 1,3,5-trimethylbenzene, nitrobenzene, anisole, chlorotoluene, o-dichlorobenzene, diethyl isophthalate, tetrahydrofuran, dimethylformamide, xylene, chloronaphthalene, decahydronaphthalene and toluene.

6. The process according to claim 1, wherein the quench is followed by further stages for cooling the reaction gas.

7. The process according to claim 6, wherein at least one of the stages for cooling the reaction gas which follow the quench is a condenser.

8. The process according to claim 1, wherein the mixture of reaction gas and quench medium is fed to a separation stage after leaving the quench.

9. The process according to claim 8, wherein the separation stage is a distillation column or a scrubber.

10. The process according to claim 1, wherein said liquid quench medium has a temperature of from 0 to 250° C. during said contacting.

11. The process according to claim 1, wherein said liquid quench medium has a temperature of from 20 to 220° C. during said contacting.

12. The process according to claim 1, wherein said inert medium is present and is present at a gas volume ratio of inert medium to amine or phosgene of from 0.0001 to 30.

13. The process according to claim 1, wherein said inert medium is present and is present at a gas volume ratio of inert medium to amine or phosgene of from 0.01 to 15.

14. The process according to claim 1, wherein said inert medium is present and is present at a gas volume ratio of inert medium to amine or phosgene of from 0.01 to 5.

* * * * *